United States Patent
Larsson et al.

(10) Patent No.: US 6,862,474 B1
(45) Date of Patent: Mar. 1, 2005

(54) IMPLANTABLE HEART STIMULATOR

(75) Inventors: Berit Larsson, Danderyd (SE); Martin Obel, Danderyd (SE)

(73) Assignee: St. Jude Medical AB, Järfälla (SE)

(*) Notice: Subject to any disclaimer, the term of this patent is extended or adjusted under 35 U.S.C. 154(b) by 236 days.

(21) Appl. No.: 10/030,931

(22) PCT Filed: Jun. 19, 2000

(86) PCT No.: PCT/SE00/01306
§ 371 (c)(1),
(2), (4) Date: Jul. 31, 2002

(87) PCT Pub. No.: WO01/03769
PCT Pub. Date: Jan. 18, 2001

(30) Foreign Application Priority Data

Jul. 9, 1999 (SE) ................................. 9902654

(51) Int. Cl.$^7$ ............................................ A61N 1/362
(52) U.S. Cl. ............................................ 607/9
(58) Field of Search ........................................ 607/1–28

(56) References Cited

U.S. PATENT DOCUMENTS

| | | |
|---|---|---|
| 4,211,235 A | 7/1980 | Keller, Jr. et al. |
| 5,330,511 A | 7/1994 | Boute |
| 5,340,361 A | 8/1994 | Sholder |
| 5,458,623 A | 10/1995 | Lu et al. |
| 5,683,428 A | 11/1997 | Franberg et al. |
| 5,713,930 A | 2/1998 | van der Veen et al. |

OTHER PUBLICATIONS

User's Manual for Pacesetter Affinity™ DR Model 530 L/R Dual Chamber Pulse Generator, pp. 52–55.

*Primary Examiner*—Scott M. Getzow
(74) *Attorney, Agent, or Firm*—Schiff Hardin LLP

(57) ABSTRACT

An implantable heart stimulator has an AV-interval generator which generates a variable AV-interval and which is provided with a predetermined basic AV-interval. The heart stimulator has a counter that counts the number of times the AV-interval is changed in response to a fusion avoidance algorithm or a stimulation threshold search algorithm during a predetermined time period. The basic AV-interval is changed if the number of times counted by the counter is greater than a predetermined value.

9 Claims, 2 Drawing Sheets

IMPLANTABLE HEART STIMULATOR

BACKGROUND OF THE INVENTION

1. Field of the Invention

The present invention relates to an implantable heart stimulator of the type which generates a variable AV interval and which is provided with a basic AV interval.

2. Description of the Prior Art

To reduce the energy consumption of heart stimulators, an automatic threshold search function is used to maintain the energy of the stimulation pulses at a level just above that which is needed to effectuate capture, cf. e.g. U.S. Pat. No. 5,458,623. A reliable detection of the evoked response, which then is necessary, is, however, not a simple matter, especially when it is desired to sense the evoked response with the same electrode as the one delivering the stimulation pulse and in particular if the sensing is performed by a unipolar electrode configuration.

A fusion beat refers typically in pacing to the ECG waveform which results when an intrinsic depolarization and a pacemaker output pulse occur simultaneously and both contribute to the electrical activation of that heart chamber. Closely related to a fusion beat is a pseudofusion beat that refers to a spontaneous cardiac depolarization occurring at or near a pulse generator output pulse. Because the stimulus occurs after the heart has spontaneously depolarized, the pacemaker output is ineffective, but it distorts the morphology of the complex on the ECG.

Today, fusion beats create a problem for the automatic threshold search function since these beats often are not detected as heart beats. Instead the heart stimulator interprets the evoked response as a loss of capture and as a consequence a backup pulse is issued and the stimulation pulse amplitude is increased. Following undetected fusion beats the heart stimulator might deliver back-up pulses (high output mode), until the next threshold search is performed. This misinterpretation by the heart stimulator of the evoked response signal will, of course, increase the current drain and decrease the lifetime of the battery and the automatic threshold search function will be disabled for some time.

U.S. Pat. No. 5,713,930 discloses a dual chamber pacing system and method with control of the AV interval. The AV interval is adjusted to provide for an optimal AV setting for a selected pacing application. A ventricular fusion test is performed, wherein variations in QT interval are monitored corresponding to variations in the AV interval. Based upon the AV-QT data, the pacemaker can determine the ventricular fusion zone where the pacemaker AV interval is substantially the same as the intrinsic conduction interval, as well as the knee where AV intervals just shorterthan the ventricular fusion zone result in full capture. One application of the dual chamber pacemaker disclosed in U.S. Pat. No. 5,713,930 is for patients with intermittent AV conduction or occasional AV block where it is desired to set the AV delay to be just greater than the natural conduction interval, so that spontaneous beats are permitted.

It should be understood that the present invention is directed to an implantable heart stimulator having, inter alia, an inhibiting function, which means that if intrinsic heart activity is detected, in the atrium or in the ventricle, no stimulation pulse is generated. This means that, using the commonly accepted terminology, the AV-interval could be started by an intrinsic atrial heart activity, a P-wave, and the started interval is then a PV-interval. Thus, instead of writing PV/AV-interval is the term AV-interval used throughout this application.

With reference to FIG. 1 the behavior of a fusion avoidance algorithm in a commercially available dual chamber heart stimulator will be described. A dual chamber heart stimulator comprising a fusion avoidance algorithm and also a threshold search algorithm (discussed below) is disclosed in e.g. "User's manual for AFFINITY™DR, Model 5330 UR, Dual-Chamber Pulse Generator with AUTOCAPTURE™ Pacing System", by Pacesetter, Ordering No. 2039782, Part. No 9192000-001, issued in 1998, pages 52–54.

FIG. 1 shows an internal electrogram (IEGM) with a normal paced heartbeat seen as the first complex. "A" and "V" designate the stimulation pulses in the atrium and in the ventricle, respectively, and "Cap" stands for capture, i.e. the applied stimulation pulse in the ventricle was successful. "AV" designates the AV-interval. The next stimulation pulse applied in the ventricle did not result in capture and to ensure safe pacing a back-up pulse is applied a predetermined interval after the stimulation pulse. The loss of capture could be the result of an intrinsic contraction at the same time as the stimulation pulse is applied which is detected as a loss of capture. Another alternative is that the stimulation threshold for the heart tissue has increased.

In order to avoid fusion the AV-interval prolonged is with a predetermined time (in the figure designated as Δ), in other words, the heart stimulator prolongs the AV-interval and waits for an intrinsic activity. In this case, as can be seen in FIG. 1, a fusion beat was detected as loss of capture in spite of the fact that it was an intrinsic beat. The AV-interval is prolonged a predetermined number of times, e.g. 3–6 times.

If instead a loss of capture is the result of an increasing stimulation threshold an IEGM illustrating that case is shown in FIG. 2. The loss of capture (LOC) in the second complex is followed be a prolonged AV-interval AV+Δ to in order to avoid a fusion beat as described above. In this case the AV-interval AV+Δ is timed out and a stimulation pulse (V) is applied to the ventricle. The applied stimulation pulse does not result in capture and a back-up pulse is applied which in turn results in capture. In this case the loss of capture was due to an increasing stimulation threshold of the heart tissue.

A threshold search algorithm may be activated by two consecutive loss of capture.

A preferred threshold search algorithm is illustrated in FIG. 2 where the AV-interval shortened to "AV-short" to override any intrinsic heart activity and the ventricular stimulation amplitude is successively stepped up by a predetermined amplitude step of e.g. 0.1–0.3 V and each unsuccessful ventricular stimulation pulse is followed by a back-up pulse. This is performed until the stimulation threshold is detected, i.e. capture is detected from the ventricular stimulation pulse, and the stimulation pulse amplitude is then set to a value that equals the stimulation threshold plus a working margin, e.g. 0.3 V.

The sinus node in the upper part of the atrium is the heart's own "pacemaker". In a normally functioning heart a depolarization wave is generated by the sinus node and conducted along the conduction system from the atrium down to the ventricle. The conduction system is briefly heart muscle cells specially adapted to depolarize at a certain frequency in the order of 0.9–2 Hz, corresponds to a heart rate of 54–120 beats per minute. If the conduction system from the sinus node in the atrium down to the ventricle does not work normally it is said that the patient has some kind of AV-block.

There are three major groups of AV-block.

A first degree AV-block is present if all atrial depolarization are conducted to the ventricle but the PQ-interval is slightly prolonged (longer than 0.21 s). There are two types of second degree AV-blocks. In second degree AV-block, Mobitz type I (also called Wenchebach block), the PR-interval increases progressively until an impulse is not conducted to the ventricle. Thereafter the cycle is repeated again.

In second degree AV-block, Mobitz type II, the length of the PQ interval is usually stable, while the blocking pattern may be regular or irregular. This means that, if the blocking pattern is regular, every second up to seventh P-wave is blocked.

A third degree AV-block (complete block) is present when there is no conduction between the atria and ventricles.

FIG. 3 shows an IEGM illustrating the behavior of a dual chamber heart stimulator provided with a fusion avoidance algorithm in combination with a stimulation threshold search algorithm on a patient with a second degree AV-block, Mobitz type 11.

The first complex represents a fusion beat followed by a back-up pulse. The AV-interval is then prolonged with A (see the fusion avoidance algorithm described above) in order to determine if the first complex was a fusion beat. In this case no intrinsic activity is detected in the ventricle because the patient has a second degree AV-block, Mobitz type II (in the following called Mobitz II-block) and thus the prolonged AV-interval is timed out and a back-up pulse is generated. Since the criteria for initiating the stimulation threshold search algorithm is two consecutive loss of capture, the search algorithm is thus initiated. The AV-interval is shortened to AV-short in order to override any intrinsic activity (see complex 3). The applied stimulation pulse was successful and capture was detected. The threshold search algorithm is thereby terminated and the AV-interval is then restored to its original programmed or basic value (see complex 4). In the next complex (complex 5) another fusion beat is present and which is detected as a loss of capture. The AV-interval is prolonged again (as in complex 2) and at the same time another Mobitz II-block is present and the sequence described above is repeated again.

One drawback with the above-described phenomena that occurs when fusion beats are present and in particular in patients with a Movitz II-block is that some patients might feel unpleasant when the AV-interval constantly is changing.

Another drawback is that several high-energy back-up pulses are delivered which consumes energy.

SUMMARY OF THE INVENTION

It is an object of the present invention to provide an implantable heart stimulator of the type described above which avoids the aforementioned disadvantages of known implantable heart stimulators.

This object is achieved in accordance with the principles of the present invention in an implantable heart stimulator having an AV-interval generator which generates a variable AV-interval and which is provided with a predetermined basic AV-interval, and a counter that counts a number of times the AV-interval is changed during a predetermined time period, the counter generating and applying an output signal to the AV-interval generator to cause the AV-interval generator to change the basic AV-interval if the number of times that the AV-interval has been changed is greater than a predetermined value.

DESCRIPTION OF THE PREFERRED EMBODIMENTS

Figure 1:
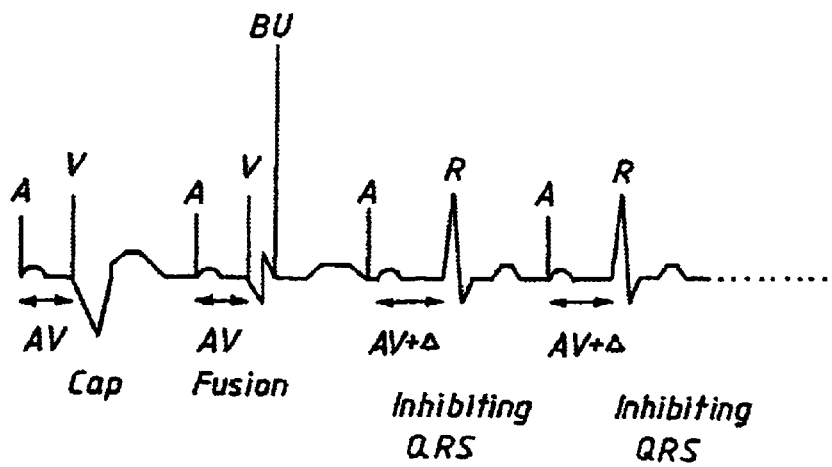
FIG. 1, as noted above, shows an IEGM illustrating a fusion avoidance algorithm used in the prior art.
Figure 2:
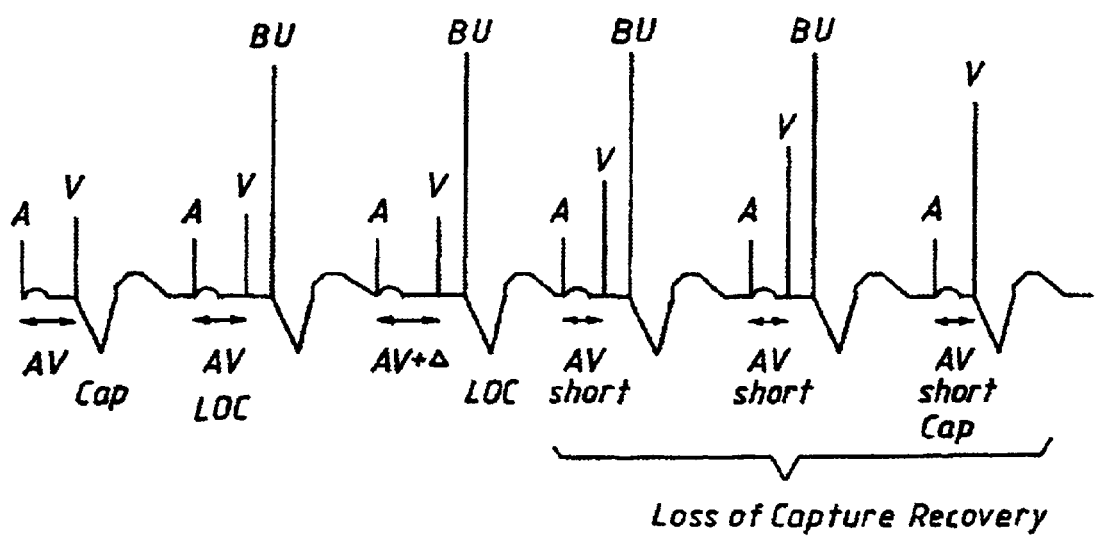
FIG. 2, as noted above, shows an IEGM illustrating a stimulation threshold search algorithm used in the prior art.
Figure 3:
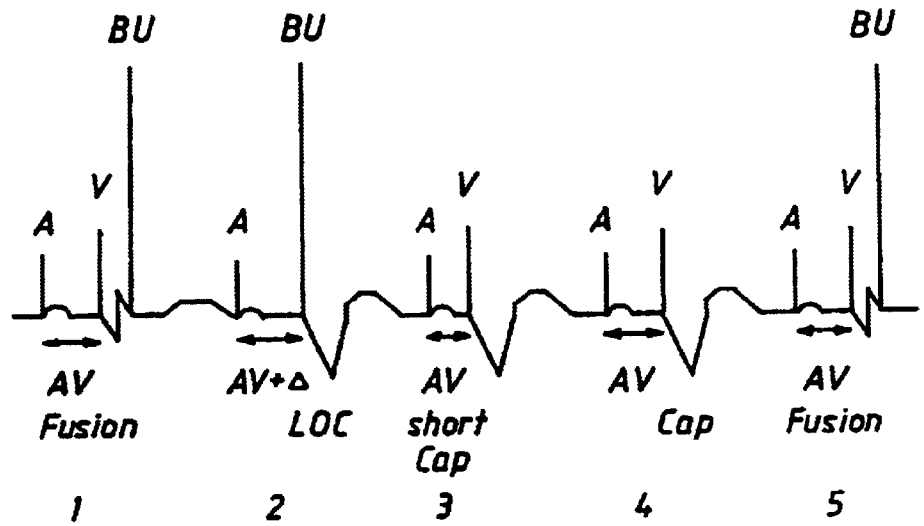
FIG. 3, as noted above, shows an IEGM illustrating the behavior of a heart stimulator provided with a fusion avoidance algorithm in combination with a stimulation threshold search algorithm on a patient with a second degree AV-block, Mobitz type 11.
Figure 4:
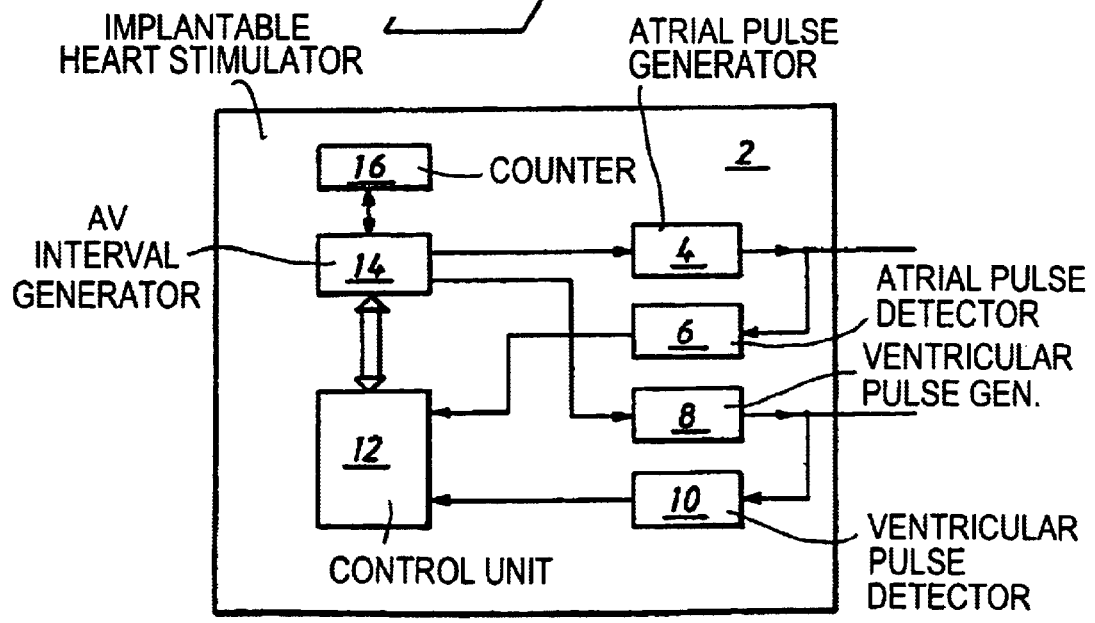
FIG. 4 shows a schematic block diagram of an implantable heart stimulator according to the invention.

FIG. 4 shows an implantable heart stimulator 2 having an atrial pulse generator 4, an atrial detector 6, a ventricular pulse generator 8 and a ventricular detector 10. The pulse generators 4,8 and the detectors 6,10 are adapted to be connected to one or many electrode leads arranged to stimulate the heart tissue and/or to detect electrical heart activity in the atrium and in the ventricle, respectively.

Those skilled in the art are aware of many different ways to arrange the electrode lead or leads. According to one embodiment is two bipolar electrode leads arranged, whereas one is arranged in the atrium and another in the ventricle. According to an alternative embodiment one multipolar electrode lead with electrode surfaces is arranged in the atrium for atrial stimulation/detection and electrode surfaces arranged in the ventricle for ventricular stimulation/detection.

To be able to implement the invention in an implantable heart stimulator it must at least have the ability to sense electrical heart activity both in the atrium and in the ventricle and to stimulate in the ventricle.

The implantable heart stimulator further has a control unit 12 connected to the atrial and ventricular detectors 6,10, an AV interval generator 14 connected to the control unit 12 and a counter 16 connected to the AV interval generator. The AV interval generator 14 is also connected to the atrial generator 4 and to the ventricular generator 8.

Upon detection of a P-wave or when the atrial stimulator generates an atrial stimulation pulse the AV interval generator starts an AV interval. The ventricular stimulator generates a ventricular stimulation pulse if the AV interval is timed out. The ventricular stimulation can be inhibited if an intrinsic ventricular event is detected prior the expiration of the AV interval.

The control unit 12 includes means, e.g. a microprocessor, to activate different algorithms related to the operation of the heart stimulator. Among these algorithms are the above mentioned stimulation threshold search algorithm and fusion avoidance algorithm.

The atrial and ventricular detectors are adapted to detect heart events in the atrium and in the ventricle, respectively. The detection may be performed in many different ways. A specific steepness of the slope of the detected electrical heart signal could be used as an indicator of a specific heart event or a predetermined integration value of a predetermined interval following an applied stimulation could also be used. Those skilled in the art are aware of many other ways to perform the detection.

When a heart event is detected by any of the detectors a signal is applied to the control unit that determines inter alia whether the detected heart event was an intrinsic heart event or if it was a stimulated heart event.

The counter 16 connected to the AV interval generator 14 counts the number of times the AV interval (AVI) is changed during a predetermined time period. This can be performed in many different ways and one way is that each time the AV interval generator makes the ventricular stimulation generator generate a ventricular stimulation pulse it compares the present AV interval (the AVI that just timed out) with the previous AV interval. If these consecutive AV intervals not are the same a count signal is generated and applied to the counter that counts the number of count signals during a predetermined time period, e.g. during the last 1–3 minutes, preferably during the last 2 minutes. If this number is greater than a predetermined value the counter 16 generates an output signal which is applied to the AV interval generator causing the basic AV interval to be changed. The predetermined value is in the interval 2–10, preferably 6. The basic AV interval is prolonged or shortened by a time in the interval of ±30 ms, preferably ±20 ms, if the number is greater than the predetermined value. In some cases it can be of interest to count even fewer AVI changes during a shorter time period, e.g. if the predetermined value is 1 then if 2 changes occur during the last one minute (or parts of a minute) the basic AVI should be changed.

A prerequisite for counting the number of times that the AVI is changed is that the AVI is timed out and as a consequence of that a ventricular stimulation pulse is generated.

Those skilled in the art of heart stimulation are aware of many different situations where the AVI can be changed. In e.g. rate responsive heart stimulators the AVI can be controlled by a signal representing the detected activity. The higher activity the shorter AVI is a relationship that is applied. It must be observed that the changes of the AVI of interest in the present application are only those that are related to the fusion avoidance algorithm and to the stimulation threshold search algorithm.

According to a preferred embodiment of the invention the basic AVI is prolonged by 20 ms if the number of changes is greater than a predetermined value during the last 2 minutes. If the situation (predetermined number of changes of the new basic AVI) is repeated again during a following time period, 1–10 minutes, the basic AVI is shortened by 20 ms. Other sequences of the changes are of course possible, e.g. first prolong the AVI with 20 ms, then go back to the original basic AVI and then shorten the AVI by 20 ms.

Although modifications and changes may be suggested by those skilled in the art, it is the intention of the inventors to embody within the patent warranted hereon all changes and modifications as reasonably and properly within the scope of their contribution to the art.

We claim:

1. An implantable heart stimulator comprising an AV-interval generator which generates a variable AV-interval and which is provided with a predetermined basic AV-interval, and a counter that counts a number of times the AV-interval is changed during a predetermined time period, said counter generating and applying an output signal to said AV-interval generator to cause said AV0-interval generator to change said basic AV-interval if said number of times is greater than a predetermined value.

2. A heart stimulator according to claim 1 wherein said AV-interval generator changes the basic AV-interval by an amount in a range of −30 to 30 milliseconds.

3. A heart stimulator according to claim 2 wherein said AV-interval generator changes the basic AV-interval by −20 ms or +20 ms.

4. A heart stimulator according to claim 1 wherein said predetermined value is in a range of 2–10.

5. A heart stimulator according to claim 1 wherein said predetermined time period is between 1 and 3 minutes.

6. A heart stimulator according to claim 1 further comprising a control unit provided with a fusion avoidance algorithm.

7. A heart stimulator according to claim 6 wherein said fusion avoidance algorithm, when activated, makes the AV-interval generator temporarily prolong the AV-interval.

8. A heart stimulator according to claim 1 further comprising a control unit provided with a stimulation threshold search algorithm.

9. A heart stimulator according to claim 8 wherein said stimulation threshold search algorithm, when activated, makes the AV-interval generator temporarily shorten the AV-interval.

* * * * *